United States Patent
Taguchi et al.

(10) Patent No.: US 10,252,964 B2
(45) Date of Patent: Apr. 9, 2019

(54) PRODUCING METHOD FOR 4-ISOPROPYL-3-METHYLPHENOL

(71) Applicant: OSAKA KASEI CO., LTD., Osaka (JP)

(72) Inventors: Yoshihiko Taguchi, Osaka (JP); Yasushi Yamagami, Ikoma (JP); Noriko Furukawa, Osaka (JP); Masaru Tobinaga, Izumi (JP)

(73) Assignee: OSAKA KASEI CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/318,546

(22) PCT Filed: Jun. 25, 2015

(86) PCT No.: PCT/JP2015/068418
§ 371 (c)(1),
(2) Date: Dec. 13, 2016

(87) PCT Pub. No.: WO2015/199202
PCT Pub. Date: Dec. 30, 2015

(65) Prior Publication Data
US 2017/0129836 A1 May 11, 2017

(30) Foreign Application Priority Data
Jun. 27, 2014 (JP) .............................. 2014-132880

(51) Int. Cl.
*C07C 37/18* (2006.01)
*C07B 61/00* (2006.01)
*C07C 39/06* (2006.01)
*A01N 31/08* (2006.01)

(52) U.S. Cl.
CPC .............. *C07C 37/18* (2013.01); *A01N 31/08* (2013.01); *C07C 39/06* (2013.01); *C07B 61/00* (2013.01)

(58) Field of Classification Search
CPC .................................................... C07C 37/18
See application file for complete search history.

(56) References Cited

U.S. PATENT DOCUMENTS 6,569,229 B1* 5/2003 Buri ................ A01N 31/08
106/15.05
2010/0331579 A1 12/2010 Heuer

FOREIGN PATENT DOCUMENTS

| CN | 101394898 A | 3/2009 |
| GB | 1344965 A | 1/1974 |
| GB | 2354771 A | 4/2001 |
| JP | 60-139634 A | 7/1985 |
| JP | 2010-533738 A | 10/2010 |
| WO | 2007/062995 A2 | 6/2007 |

OTHER PUBLICATIONS

Han et al. "Negishi Coupling of Secondary Alkylzinc Halides with Aryl Bromides and Chlorides" Journal of the American Chemical Society, 2009, vol. 131, pp. 7532-7533.*
Erickson et al. "Thallium(III)-induced bromination of meta-substituted anisoles" Journal of the Chemical Society D: Chemical Communications, 1971, 1596-1597.*
Hodgson et al. "CCLXXIII.—Nitrosation of phenols. Part III. Nitrosation of 4-halogeno-o- and -m-cresols and oximation of the 4-halogeno-2 : 5-toluquinones" Journal of the Chemical Society, 1926, vol. 129, pp. 2036-2040.*
T.W. Greene, et al; "Protective Groups in Organic Synthesis Third Ediction", 1999, pp. 249-250.
Chong Han, et al; "Negishi Coupling of Secondary Alkylzinc Halides with Aryl Bromides and Chlorides", J. Am. Chem. Soc. vol. 131, pp. 7532-7533; Published on Web May 14, 2009.
Ranjan Jana, et al; "Advances in Transition Metal (Pd,Ni,Fe)-Catalyzed Cross-Coupling Reactions Using Alkyl-organometallics as Reaction Partners", Chemical Reviews, vol. 111, pp. 1417-1492; Published Feb. 14, 2011.
Amruta Joshi-Pangu, et al; "Nickel-Catalyzed Negishi Cross-Coupling Reactions of Secondary Alkylzinc Halides and Aryl Iodides", Organic Letters, vol. 13, No. 5, pp. 1218-1221; Published on Web Feb. 10, 2011.
International Search Report dated Sep. 15, 2015; PCT/JP2015/068418.
R.A.B. Bannard, et al; "The Synthesis of Two Isomeric Thymols", Canadian Journal of Chemistry, vol. 34, No. 10, pp. 1464-1470, 1956.
Jeanne L. Bolliger, et al; "[Pd(Cl)$_2${P(NC$_5$H$_{10}$)(C$_6$H$_{11}$)$_2$}$_2$]—A Highly Effective and Extremely Versatile Palladium-Based Negishi Catalyst that Efficiently and Reliably Operates at Low Catalyst Loadings", Chemistry-European Journal, vol. 16, No. 36, pp. 11072-11081.
Ganapati D. Yadav, et al; "Zirconia-Modified Superacid UDCaT-5: An Efficient and Versatile Catalyst for Alkylation Reactions", Synthetic Communications, vol. 38, No. 15, pp. 2684-2691; Published online Sep. 9, 2008.

* cited by examiner

*Primary Examiner* — Joseph R Kosack
(74) *Attorney, Agent, or Firm* — Ladas & Parry LLP

(57) ABSTRACT

The main object of the present invention is to provide a producing method for a 4-isopropyl-3-methylphenol which may be selectively produced, easily refined, and with less odor and coloration. The present invention achieves the object by providing a producing method for a 4-isopropyl-3-methylphenol characterized in that a 4-halogenated-3-methylphenol or a phenol derivative thereof is reacted with an isopropyl metal compound under presence of a catalyst and a solvent.

8 Claims, No Drawings

PRODUCING METHOD FOR 4-ISOPROPYL-3-METHYLPHENOL

TECHNICAL FIELD

The present invention relates to a producing method for a 4-isopropyl-3-methylphenol. In specific, the present invention relates to a producing method that is capable of producing a 4-isopropyl-3-methylphenol in a good yield. Moreover, the present invention relates to a producing method that is capable of producing a 4-isopropyl-3-methylphenol with less odor and coloration efficiently.

BACKGROUND ART

An isopropylmethylphenol is widely used for products such as medicaments, quasi-drugs and cosmetics, as their agents such as an antibacterial agent, a bactericidal agent, and an antiseptic. Isomers exist in an isopropylmethylphenol; among them, a 4-isopropyl-3-methylphenol (hereinafter described as p-thymol in some cases) has characteristics such that its antibacterial and bactericidal activities are strong, as well as its toxicity against skin irritation is low, and it is colorless and odorless.

A method in which an m-cresol is reacted with propylene under presence of a catalyst so as to be isopropylated is known as a producing method for an isopropylmethylphenol. In this method, a 4-isopropyl-3-methylphenol, a 6-isopropyl-3-methylphenol (hereinafter described as o-thymol in some cases), a 5-isopropyl-3-methylphenol (hereinafter described as m-thymol in some cases), and a 2-isopropyl-3-methylphenol (hereinafter described as vic-thymol in some cases) that are isomers are produced. Accordingly, a 4-isopropyl-3-methylphenol has been presently produced by reacting an m-cresol with propylene under presence of a catalyst so as to obtain a mixture of the isomers, and then these mixture undergoing refinement controls such as isomerization, distillation, extracting, and crystallization, in general.

As for a producing method for an isopropylmethylphenol from an m-cresol and propylene, for example, a method using calcium oxide as a catalyst (Patent Document 1), a method using a metal sulfate and γ-alumina as a catalyst (Patent Document 2), and a method using a catalyst solution including a zinc bromide, hydrogen bromide and water (Patent Document 3) are known.

Also, a method in which a phosphoric acid is brought to coexist in a reaction of an m-cresol with propylene is known. For example, reported method is such that a phosphoric compound selected from a group consisting of a phosphoric anhydride, condensed phosphoric acid and salt thereof, and a phosphoric acid and salt thereof is brought to coexist in producing alkyl phenols by reacting phenols such as an m-cresol with olefins such as a propylene, using an activated clay or acid clay as a catalyst in liquid phase (Patent Document 4). Further, a method also reported is such that an m-cresol is reacted with propylene under presence of a catalyst that is a solid phosphate catalyst in which at least one kind of a carrier selected from a group consisting of silica-alumina, diatomaceous earth, and silica-titania are supported by a phosphoric acid at the specific ratio; the reaction is conducted in a heated liquid phase and under condition of the specific propylene pressure, so as to produce thymols that has a p-thymol and o-thymol mainly and the production ratio of o-thymol/p-thymol is 3/1 or less (Patent Document 5).

Also, reported method is such that an m-toluidine is isopropylated under presence of a sulfuric acid so as to be a methyl-4-isopropylaniline, then the methyl-4-isopropylaniline is diazo-decomposed or hydrolyzed under high temperature and high pressure to produce a 4-isopropyl-3-methylphenol (Patent Document 6).

CITATION LIST

Patent Documents

Patent Document 1: Japanese Patent Application Laid-Open (JP-A) No. S45-015491
Patent Document 2: JP-A No. S46-003053
Patent Document 3: German Patent No. 2139622
Patent Document 4: JP-A S41-016781
Patent Document 5: JP-A S61-052130
Patent Document 6: Chinese Patent Application Laid-Open No. 103044205

SUMMARY OF INVENTION

Technical Problem

The object for the methods disclosed in Patent Documents 1 to 3 is all to produce an o-thymol; also, the selectivity of the reaction is not enough; thus the isomers such as an o-thymol, p-thymol, m-thymol, and diisopropyl cresol are produced which makes difficult to produce the p-thymol selectively. Also, the reactivity itself is also insufficient.

An improvement for the reactivity may be expected by the method disclosed in Patent Document 4; however, the selectivity of the reaction is not described and thus the selective production of the p-thymol is still difficult.

In contrast, the method disclosed in Patent Document 5 allows a product having the p-thymol and o-thymol mainly to be obtained, as well as inhibits the m-thymol from being produced. However, it is yet insufficient at the point to produce only the p-thymol selectively; it is far short for obtaining the p-thymol at high selective rate and in a high yield at the reaction stage without depending on the refinement.

Also, another problem is that the separation of p-thymol, o-thymol, and m-thymol is difficult since their boiling points are close.

As described above, a producing method for a p-thymol selectively has not been found out conventionally, and its emergence has been strongly demanded.

In addition, another problem in conventional methods is that a propylene gas is used as the raw material so that the pressure container such as an autoclave is necessary for the reaction, which takes costs for the facility.

Furthermore, according to the consideration by the present inventors, it has been found out that the conventional method has had problem such that odor and coloration have remained in the obtained p-thymol. The reason therefor is considered to be because the materials that may become reasons for the odor and coloration exist a lot in the conventional method such as an m-cresol as its raw material, and an o-thymol, m-thymol, and diisopropyl cresol as its products. Specifically, it is presumed that the reason is due to the above-described difficulty in separating the p-thymol, o-thymol, and m-thymol. Large load may be applied to the refinement when trying to solve this problem.

For this problem, according to the method disclosed in Patent Document 6, the p-thymol may be produced without creating isomers as byproducts. However, other byproducts and unreacted materials besides thymols are a lot in this method; thus the highest yielding rate remains 50%. Accordingly, the problem has been yet unsolved at the point of the load applied to the refinement for obtaining the p-thymol. Also, it is considered that this method is also economically not so practical since the number of the production step is a lot. Further, the problem of the odor and coloration has been yet unsolved along with the low level in a yield.

The present invention has been made in view of the above problematic points, and the object thereof is to provide a producing method capable of selectively producing a 4-isopropyl-3-methylphenol. Further, the object of the present invention is to provide a producing method capable of efficiently producing a 4-isopropyl-3-methylphenol that is easily refined and with less odor and coloration.

Solution to Problem

The present inventors have thoroughly researched in order to solve the problems; as the result, it has become clear that a 4-isopropyl-3-methylphenol at high selective rate and in high yielding rate may be obtained by using an isopropyl metal compound but not propylene as the raw material, and reacting this isopropyl metal compound with a 4-halogenated-3-methylphenol under presence of a catalyst and solvent; the present invention has been achieved thereby.

In other words, the present invention provides a producing method for a 4-isopropyl-3-methylphenol characterized in that a 4-halogenated-3-methylphenol or a phenol derivative thereof is reacted with an isopropyl metal compound under presence of a catalyst and a solvent.

In the present invention, a 4-halogenated-3-methylphenol or a phenol derivative thereof is reacted with an isopropyl metal compound under presence of a catalyst and a solvent, so that the creation of isomers o-thymol and m-thymol as the byproducts may be inhibited and thus the 4-isopropyl-3-methylphenol may be produced at high selective rate and in high yielding rate. As the result, the 4-isopropyl-3-methylphenol with less odor and coloration may be obtained.

In the invention, the 4-halogenated-3-methylphenol is preferably a 4-bromo-3-methylphenol. The reason therefor is because the 4-bromo-3-methylphenol is high in reactivity and may be reasonably obtained.

Also, in the present invention, the isopropyl metal compound is preferably an isopropyl zinc bromide. The reason therefor is because the isopropyl zinc bromide is high in reactivity.

Further, in the present invention, the catalyst preferably includes one kind or two kinds or more selected from palladium, nickel, ruthenium, iron and copper. These transition metal catalysts may be applied to the reaction.

Also, in the present invention, the reaction is preferably conducted under presence of a ligand having a biarylphosphine skeleton. The ligand has appropriate bulkiness that makes easy to introduce an isopropyl group to the position 4 adjacent to the methyl group at the position 3 having a steric hindrance of the 4-halogenated-3-methylphenol, and thus is useful for the reaction. Also, the ligand is bulky so that the reaction may be selectively proceeded without protecting a phenolic hydroxy group and thus the production steps may be greatly simplified.

In the above case, the ligand preferably has a biaryldialkylphosphine skeleton; also, the ligand is preferably one kind or a mixture of two or more kinds selected from a 2-dicyclohexylphosphino-2',6'-diisopropoxybiphenyl, a 2-dicyclohexylphosphino-2',6'-dimethoxybiphenyl, and a 2-dicyclohexylphosphino-2',6'-bis(N,N-dimethylamino)biphenyl.

The reason therefor is because these ligands have appropriate bulkiness, so that the selectivity of the reaction is favorable for the same reason above.

Also, in the present invention, the solvent is preferably a solvent including ether that is capable of dissolving the isopropyl metal compound.

Further, in the present invention, it is preferable that the catalyst and the ligand are mixed with the solvent, and then the 4-halogenated-3-methylphenol and the isopropyl metal compound are added to the mixed solution.

Also, in the present invention, at least either of the catalyst and the ligand is preferably fixed to a solid support. The reason therefor is because if the catalyst and ligand are fixed to the solid support, these may be easily separated after the reaction.

Also, the present invention provides a 4-isopropyl-3-methylphenol composition produced in accordance with the above-described producing method; the 4-isopropyl-3-methylphenol composition comprising a 4-normalpropyl-3-methylphenol in a range of 0.1 mass % to 10 mass % with respect to a 4-isopropyl-3-methylphenol.

Also, the present invention provides an antibacterial or bactericidal composition comprising a 4-isopropyl-3-methylphenol produced in accordance with the above-described producing method. A composition including the 4-isopropyl-3-methylphenol as an antibacterial agent and bactericidal agent may be obtained.

Advantageous Effects of Invention

The present invention produces the effect capable of producing a 4-isopropyl-3-methylphenol at high selective rate and in high yielding rate, and obtaining a 4-isopropyl-3-methylphenol with less odor and coloration. Also, the present invention produces the effect capable of producing a 4-isopropyl-3-methylphenol at high selective rate and in high yielding rate without protecting a phenolic hydroxy group.

DESCRIPTION OF EMBODIMENTS

A producing method for the 4-isopropyl-3-methylphenol, antibacterial composition and bactericidal composition of the present invention will be hereinafter described in details.

A. Producing Method for 4-isopropyl-3-methylphenol

The producing method for the 4-isopropyl-3-methylphenol of the present invention is a method characterized in that a 4-halogenated-3-methylphenol or a phenol derivative thereof is reacted with an isopropyl metal compound under presence of a catalyst and a solvent.

The present invention is a producing method for a 4-isopropyl-3-methylphenol utilizing a cross coupling reaction. Specifically, it is a method for forming a carbon-carbon bond newly in the manner that a 4-halogenated-3-methylphenol or a phenol derivative thereof is reacted with an isopropyl metal compound under presence of a catalyst and a solvent, so that an isopropyl group that is a bulky second alkyl group is bonded to an aromatic ring (aromatic compound).

Accordingly, the present invention allows selective production of the 4-isopropyl-3-methylphenol. Production of an o-thymol and m-thymol as the isomers of the 4-isopropyl-3-methylphenol may be inhibited thereby, and thus the 4-isopropyl-3-methylphenol may be obtained in high yielding rate.

Also, these isomers are difficult to be separated since the boiling points are close to that of the 4-isopropyl-3-methylphenol, but the production of the o-thymol and m-thymol are inhibited in the present invention, so that the loss in the refinement may be decreased and the refinement steps may be simplified.

Further, the method of the present invention does not use an m-cresol as a raw material like a conventional method; also, the production of the o-thymol and m-thymol may be inhibited so that the amount of the materials that may be the cause of the odor and coloration is small, and thus the 4-isopropyl-3-methylphenol with less odor and coloration may be obtained. The conventional method has used an m-cresol as a raw material; thus the isopropylation of all o-position, m-position, and p-position of the m-cresol has been proceeded; products of the o-position that is most stable among them has been a lot, and the isopropylation of the intended p-position has been proceeded in only a small amount. The method of the present invention uses the 4-halogenated-3-methylphenol or a phenol derivative thereof in which only the p-position of the m-cresol is halogenated in advance, so that the production of the o-thymol and m-thymol may be inhibited.

Also, unlike the conventional method, propylene gas is not used as the raw material, so that the 4-isopropyl-3-methylphenol may be produced without using a pressure container such as an autoclave, and thus the production cost may be reduced as well.

Incidentally, the fact that the secondary alkalization reaction to the aromatic series is proceeded if the secondary zinc alkyl halide are reacted with an aromatic halide such as an aromatic bromide and aromatic chloride under the presence of a transition metal catalyst, is widely known as Negishi coupling reaction, and various specific reaction examples have been reported (such as Ranjan Jana, et al., Chemical Reviews 2011, 111, 1417-1492; Chong Han and Stephen L. Buchwald, J. Am. Chem. Soc. 2009, 131, 7532; and Amruta Joshi-Pangu et al., Organic Letters 2011, Vol. 3, No. 5, 1218-1211).

However, there is no case in which this Negishi coupling reaction is applied to the reaction for synthesizing the 4-isopropyl-3-methylphenol intended in the present invention by using a 4-halogenated-3-methylphenol and an isopropyl metal compound as the raw materials.

Here, "the 4-halogenated-3-methylphenol" used as the raw material in the producing method of the present invention is the one including a derivative of the compound. Examples of the 4-halogenated-3-methylphenol derivative may include a compound in which the hydroxy group of the compound is protected by a protective group. Incidentally, in the present descriptions, the compound in which the hydroxy group of the compound is protected by a protecting group may be referred to as the phenol derivative of the compound in some cases.

In the present invention, when using the phenol derivative, a reaction to take out the protective group (deprotection) may be conducted at the arbitrary stage before producing the intended 4-isopropyl-3-methylphenol. The method for the deprotection may be in accordance with the rule depending on the kind of the protective group to be used.

The protective group of the hydroxy group in the phenol derivative is not particularly limited, and may be a protective group of the hydroxy group to be used for an usual organic synthesis; specific examples of the protective group may include an ether system having a protective group such as a methyl group, benzyl group, p-methoxybenzyl group, t-butyl group; an acetal system having a protective group such as a methoxymethyl group, 2-tetrahydropyranyl group, and ethoxyethyl group; an acyl system having a protective group such as an acetyl group, pivaloyl group, and benzoyl group; and a silyl ether system having a protective group such as trimethylsilyl, triethylsilyl, t-butyldimethylsilyl, triisopropylsilyl, and t-butyldiphenylsilyl. Among them, an ether system protective group is preferable as the protective group of the hydroxy group; above all, a methyl group is preferable.

Incidentally, as described above, while the phenol derivative may be used as the raw material in the producing method of the present invention, intended 4-isopropyl-3-methylphenol may be obtained without protecting the hydroxy group by appropriately selecting and using the catalyst, and ligand that may be arbitrary used, as described later. Accordingly, in the viewpoint of simplifying the production step, the 4-halogenated-3-methylphenol not having a protective group is preferred as the raw material.

The case of using the 4-halogenated-3-methylphenol as the raw material will be hereinafter described. Incidentally, as described above, the same may be applied to the case of using the 4-halogenated-3-methylphenol derivative. Also, a 4-halogenated-3-methylphenol derivative other than the phenol derivative is not excluded from the technical scope of the present invention as long as the production of a 4-isopropyl-3-methylphenol is possible thereby with application of the technical idea described below.

The producing method for the 4-isopropyl-3-methylphenol of the present invention will be hereinafter described in details.

(1) 4-halogenated-3-methylphenol

Examples of the 4-halogenated-3-methylphenol may include a 4-fluoro-3-methylphenol, 4-chloro-3-methylphenol, 4-bromo-3-methylphenol, and 4-iodo-3-methylphenol. Above all, in the viewpoint of handleability, a 4-chloro-3-methylphenol, 4-bromo-3-methylphenol, and 4-iodo-3-methylphenol are preferable. Further, a 4-bromo-3-methylphenol and 4-iodo-3-methylphenol are preferable for their high reactivity; a 4-bromo-3-methylphenol is particularly preferable in the viewpoints of reactivity and cost.

The synthesis method for the 4-halogenated-3-methylphenol is not particularly limited, but a method of halogenating an m-cresol is preferable in the viewpoints of cost, yield, and quality. Specifically, the method in which an m-cresol is reacted with a metal halide is preferable. For example, the 4-bromo-3-methylphenol is preferably the one in which the m-cresol is brominated. A conventionally known method may be appropriately applied to the synthesis condition and refinement method. Also, the 4-halogenated-3-methylphenol is commercially available so that the commercialized product may be obtained and used.

(2) Isopropyl Metal Compound

An isopropyl metal compound is used as an organic metal reagent in the reaction of the present invention. The isopropyl metal compound may be the one having a carbon-metal bond, but above all, an isopropyl metal halide is preferable. A compound represented by the following formula (1) is specifically exemplified as the isopropyl metal halide.

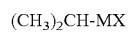

(In the formula, M represents a metal selected from zinc, magnesium, aluminum, zirconium and lithium; X represents a halogen atom selected from a chlorine atom, bromine atom and iodine atom.)

As for the isopropyl metal halide, it is preferable that zinc or magnesium is selected as the metal M in the formula (1), and zinc is more preferable. Also, as for the halogen X in the formula (1), bromine or iodine is preferable, and bromine is more preferable. In other words, an isopropyl zinc bromide is particularly preferable. The reactivity of the coupling reaction regarding to the present invention tends to be improved by selecting the M and X in the formula (1) as described above, thus the selection is preferable; further, the reactivity when using one containing palladium as the later-described catalyst tends to be improved. Also, selection and usage of the appropriate isopropyl metal compound in the producing method of the present invention may allow favorable conduction of the reaction at comparatively low temperature and under condition of normal pressure, without setting the conditions such as under high temperature and high pressure.

Incidentally, examples of the isopropyl metal compound other than the halide may include diisopropyl zinc and diisopropyl magnesium.

The preparation method for the isopropyl zinc halide is not particularly limited, but example thereof may include a preparation method by means of a transmetalation of isopropyl magnesium halide and zinc halide. The producing method for the isopropyl zinc bromide is not particularly limited, and a conventionally known method is applicable; for example, a method is described in P. Knochel, Comprehensive Org. Syn., Vol. 1, 211 and C. F. Malosh et al, J. Am. Chem. Soc., 126, 10240 (2004). Above all, the isopropyl zinc bromide is preferably prepared from isopropyl magnesium bromide and zinc bromide.

Incidentally, metal zinc and lithium chloride may be used for the preparation instead of the zinc bromide. Also, the isopropyl zinc halide such as isopropyl zinc bromide is commercially available, thus a commercialized product may be obtained and used.

The amount of the isopropyl metal compound to be used for the reaction is not limited, but with respect to 1 mol of the 4-halogenated-3-methylphenol, the amount is usually in a range of 0.9 mol to 3 mol, preferably in a range of 1 mol to 2 mol, more preferably in a range of 1.0 mol to 1.5 mol, further more preferably in a range of 1.0 mol to 1.3 mol, and particularly preferably in a range of 1.0 mol to 1.1 mol. Here, the amount of the isopropyl metal compound signifies the "mol equivalent" in the cross coupling reaction with respect to the 4-halogenated-3-methylphenol. The adding order of each raw material and the conditions for reaction may be optimized in order to allow the reaction of the present invention to be proceeded while setting the amount of isopropyl metal compound to be in the above range.

(3) Catalyst

The catalyst may be the one applicable to the cross coupling reaction, and example thereof may include a transition metal catalyst. Examples of the transition metal contained in the transition metal catalyst may include elements belonging to the groups 8 to 11 in the periodic table (IUPAC); above all, one kind or two kinds or more selected from palladium, nickel, ruthenium, iron and copper is preferable. In particular, palladium is preferable for its excellence in catalysis.

Examples of the transition metal catalyst may include an organic metal compound. The organic metal compound is not particularly limited if it allows a complex in which a ligand is coordinated with the transition metal to be obtained by mixing the compound with the later described ligand in a solvent. As for such organic metal compound, the anion kind that bonds to a metal ion is not particularly limited if it does not interfere the coordination of a ligand with the transition metal, but example thereof may include a hydrocarbon group with carbon number 1 to 20 having an anion group. Examples of the anion group bonded to the hydrocarbon group may include carbanion, sulfate ion, cyanide ion, nitro ion, halogen (fluorine, chlorine, bromine, iodine) ion. Above all, aliphatic carbanion with carbon number 1 to 20 is preferable. Specific examples thereof may include acetate ion, acetylacetonate, propionate ion, and pivalate ion.

The valence of the metal varies in accordance with the kind of the metal, thus is not particularly limited. For example, the valence of palladium may be 0 and may be 2, but preferably 2 among them. In particular, palladium acetate (Pd(OAc)$_2$) is preferably used.

The catalyst may be used singly and may be used in combination.

Also, the catalyst may be fixed to a solid support. The reason therefor is that if the catalyst is fixed to a solid support, the catalyst may be easily separated and collected after the reaction, and may be reused as well. The producing method of the present invention has extremely high reaction selectivity, and features the characteristic of inhibiting production of isomers and byproducts. Accordingly, if the catalyst is fixed, the 4-isopropyl-3-methylphenol may be obtained in high yielding rate and high purity by removing the solvent from the solution after the reaction.

Examples of the solid support may include silica, alumina, and synthetic zeolite.

A conventionally known method is applicable to the method for fixing the catalyst to the solid support, and examples thereof may include a method for fixing the catalyst to the solid support with a linker.

Incidentally, as for the fixation of the catalyst, only the catalyst may be fixed, and a complex may be formed along with the later described ligand and then the complex may be fixed.

The usage amount of the catalyst may be appropriately selected in accordance with the conditions for the reaction such as the reaction temperature, but is preferably in a range of 0.1 mol % to 2 mol % with respect to the 4-halogenated-3-methylphenol.

(4) Ligand

It is preferable that a ligand coexists in the reaction of the present invention. In other words, the 4-halogenated-3-methylphenol is preferably reacted with the isopropyl metal compound under presence of a catalyst, ligand, and solvent.

An example of the producing method for the 4-isopropyl-3-methylphenol of the present invention is described as follows. In the cross coupling reaction, as described below, it is considered that the 4-isopropyl-3-methylphenol may be obtained through oxidative addition, transmetalation, and reductive elimination. Incidentally, in the following reaction scheme, L represents a ligand.

[Chemical Formula 1]

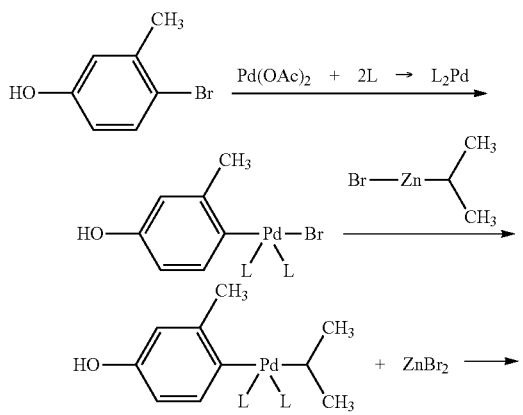

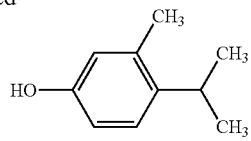

The ligand is not particularly limited if it can be coordinated to the transition metal of the transition metal catalyst; above all, the ligand preferably has a bulky structure. The reason therefor is because it is considered that the reductive elimination may be promoted by selecting the bulky ligand. Thereby, the reaction may be conducted under a mild reaction condition such as a room temperature, and the 4-isopropyl-3-methylphenol may be obtained in high yielding rate. Further, the bulkiness of the ligand may allow the reaction to be proceeded selectively without protecting a phenolic hydroxy group that has high reactivity. Accordingly, protection and deprotection of the hydroxy group become unnecessary, which greatly simplifies the step.

As for such ligand, a ligand having a biarylphosphine skeleton is preferably used. The reason therefor is because the ligand having a biarylphosphine skeleton has appropriate bulkiness when the ligand forms a complex structure with the catalyst, so that it becomes easy to introduce an isopropyl group to the position 4 adjacent to the methyl group at position 3 having a steric hindrance of the 4-halogenated-3-methylphenol.

The biaryl structure of the biarylphosphine skeleton is preferably biphenyl.

The binding position of a phosphorus atom in the biaryl structure is not particularly limited, but taking biphenyl for example, it is preferably the position represented in the following formula (2). The reason therefor is because the ligand has appropriate bulkiness and the selectivity of reaction is favorable for the same reasons above.

[Chemical Formula 2]

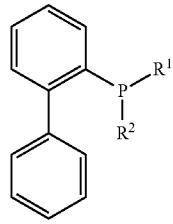

(2)

(In the formula, $R^1$ and $R^2$ each independently represent an arbitrary hydrocarbon group.)

The aromatic ring in the biaryl structure may have a substituent. The substituent preferably has an electron donor. The selectivity of reaction and reactivity regarding to the present invention is further optimized when the aromatic ring in the biaryl structure has an electron donating substituent, and the yielding rate of the 4-isopropyl-3-methylphenol to be obtained is likely improved. Examples of the electron donating substituent may include an alkyl group, alkoxy group, and amino group. Above all, an alkyl group with carbon number 1 to 4, an alkoxy group with carbon number 1 to 4, and an alkylamino group with carbon number 1 to 4 are preferable. The number of the substituent is not particularly limited, but is usually 1 to 4, and preferably 1 to 3. The preferable biaryl structure having the substituent is specifically diisopropylbiaryl, dimethoxybiaryl, and bis(dimethylamino)biaryl.

The hydrocarbon group to be bonded to a phosphorus atom at the phosphine position in the biarylphosphine skeleton (corresponding to $R^1$ and $R^2$ in the formula (2)) is not particularly limited; it may be an aliphatic hydrocarbon group and may be an aromatic hydrocarbon group; above all, an aliphatic hydrocarbon group is preferable. Examples of the aliphatic hydrocarbon group may include a chain (strait or branched) alkyl group and a cycloalkyl group; above all, a branched alkyl group or a cycloalkyl group is preferable. The reason therefor is because the bulkiness of the ligand is appropriate when the hydrocarbon group to be bonded to a phosphorus atom is a branched alkyl group or a cycloalkyl group, so that the selectivity of reaction is favorable for the same reasons above. For example, if $R^1$ and $R^2$ in the formula (2) are both cycloalkyl group, the bulkiness of the ligand becomes optimum.

The branched alkyl group is not particularly limited, but a t-butyl group is preferable. The cycloalkyl group is not particularly limited, but a cyclohexyl group is preferable. Also, the cycloalkyl group may be the one in which the hydrogen that constitutes the ring is substituted with an alkyl group with carbon number 1 to 4.

The cycloalkyl group as the hydrocarbon group bonded to a phosphorus atom may be one and may be two, but preferably two. In other words, the phosphine position is preferably a dicycloalkylphosphino group.

Accordingly, the ligand preferably has a biaryldialkylphosphine skeleton. Further, the ligand having the biaryldialkylphosphine skeleton is preferably a biphenyldialkylphosphine in which the biaryl structure is biphenyl; also, it is preferably a biaryldicycloalkylphosphine in which the dialkyl position is cycloalkyl.

In these manners, the selectivity of reaction and reactivity regarding to the present invention is tend to be optimized by selecting the ligand that has an appropriate bulky structure. On the other hand, if not so bulky ligand is used, the reaction selectivity may be diminished, and the reaction without protecting the hydroxy group of the raw material 4-halogenated-3-methylphenol may be deteriorated in some cases. Also, if a ligand that has exceedingly bulky structure is used, a complex may not be formed well with a catalyst, and the reactivity may be deteriorated since the complex cannot interoperate with the reaction point in some cases.

Specific examples of the ligand may include 2-dicyclohexylphosphino-2',6'-diisopropoxybiphenyl (hereinafter referred to as RuPhos in some cases), 2-dicyclohexylphosphino-2',6'-dimethoxybiphenyl (hereinafter referred to as SPhos in some cases), 2-dicyclohexylphosphino-2',6'-bis(N,N-dimethylamino)biphenyl (hereinafter referred to as CPhos in some cases), and 2-dicyclohexylphosphino-2',4',6'-triisopropylbiphenyl (hereinafter referred to as XPhos in some cases). The ligand may be one kind, and may be a mixture of two kinds or more.

Above all, the ligand is preferably one kind or a mixture of two kinds or more selected from RuPhos, SPhos and CPhos. The reason therefor is because the reaction speed and selectivity thereof are favorable.

Also, the ligand may be fixed to a solid support. The reason therefor is that if the ligand is fixed to a solid support, the ligand may be easily separated and collected after the reaction and may be reused as well. Examples of the solid support may include silica, alumina, and synthetic zeolite.

Examples of the method for fixing the ligand to the solid support may include a method for fixing a ligand to a solid support with a linker and a method for directly fixing the ligand to a solid support.

The usage amount of the ligand with respect to the catalyst is preferably in a range of 100 mol % to 300 mol %, and more preferably 250 mol % or less. The reason therefor is because the reaction speed may be delayed if the amount of ligand is small, and the cost may be high if the amount of the ligand is large.

The transition metal catalyst and ligand are mixed in a solvent. On this occasion, the catalyst and ligand may be mixed in advance outside the reaction system, and the catalyst and ligand may be mixed in the reaction system.

(5) Solvent

The solvent is not particularly limited if it does not interfere the reaction; example thereof may include aprotonic polar solvent. The aprotonic polar solvent may be the one that is liquid at normal temperature; specific example thereof may include ethers such as tetrahydrofuran (THF), tetrahydropyran, dioxane, and diethyl ether; carbonates such as dimethyl carbonate (DMC), ethyl methyl carbonate (EMC), diethyl carbonate (DEC), and propylene carbonate (PC); esters such as ethyl acetate and butyl acetate; and aromatic hydrocarbons such as toluene and xylene. Above all, the solvent is preferably capable of dissolving the isopropyl metal compound. In particular, ethers that can dissolve the isopropyl metal compound are preferable. The solvent may be used singly and may be used in combination.

The usage amount of the solvent is appropriately adjusted in accordance with the reaction format and reaction scale.

(6) Reaction

The reaction temperature in the present invention is not particularly limited, but may be set in a range of −10° C. or more and the boiling point of the solvent or less for example. The lower limit of the reaction temperature is preferable 0° C. or more and more preferably 10° C. or more. If the reaction temperature is low, the reaction speed may be delayed and side reaction may be easily caused in some cases. Also, the upper limit of the reaction temperature is preferably 100° C. or less, more preferably 80° C. or less, and further more preferably 60° C. or less. The reason therefor is because the side reaction such as production of an isomer 4-n-propyl-3-methylphenol is easily caused if the reaction temperature is high.

The reaction of the 4-halogenated-3-methylphenol with the isopropyl metal compound under presence of a catalyst and solvent is an exothermic reaction; thus, when the temperature of the reaction system rises due to the insufficient heat removal, the temperature rise is preferably suppressed by controlling the concentration and adding speed of each component, and the adding timing, by improving the stirring efficiency of the reactor and by applying a cooling apparatus.

The reaction time is appropriately selected in accordance with the kinds of the 4-halogenated-3-methylphenol and isopropyl metal compound, the kind of the catalyst and ligand, the reaction temperature, the adding method for each raw material, and the reaction method (batch method, continuous method).

The reaction is preferably conducted under normal pressure. The reason therefor is because the pressure container for reducing pressure and applying pressure is not necessary if the reaction is conducted under normal pressure, which may decrease the production cost.

Incidentally, the reaction is preferably conducted in an inert gas atmosphere from the viewpoints of inhibiting the reaction interference and side reactions, and safety for using flammable solvent. Specific examples of the inert gas may include nitrogen and argon.

On the occasion of conducting the reaction, the adding order and adding timing of each raw material are not particularly limited if the reaction is proceeded in accordance with the above-mentioned reaction scheme, and may be arbitrarily set. Specifically, appropriate mixture of the 4-halogenated-3methylphenol, isopropyl metal compound, catalyst and ligand in a solvent may proceed the reaction, but the catalyst and ligand are preferably mixed in advance in the solvent. Incidentally, when using the ligand fixed to a solid support, the fixed catalyst is usually produced in advance.

As for the method for mixing each raw material, all the raw materials may be added concurrently and mixed together, but it is preferable to add each raw material sequentially; specific example of the adding order is as follows. Incidentally, in the following, all the raw materials are described as it is respectively dissolved in the solvent (including suspension), but the intended material may be used as it is but not dissolved in the solvent. Also, as for the addition of each raw material, whole amount of the raw material may be added at one time, may be added with time by the manner such as droplet, and may be added in a plurality of times.

(A) The mixture of catalyst and ligand, the solution of isopropyl metal compound are added to the solution of 4-halogenated-3-methylphenol.

(B) The mixture of catalyst and ligand and the solution of 4-halogenated-3-methylphenol are added to the solution of isopropyl metal compound.

(C) The solution of 4-halogenated-3-methylphenol and the solution of isopropyl metal compound are added to the mixture of catalyst and ligand.

In the mixing order case (A), the 4-halogenated-3-methylphenol is dissolved in the solvent and thereafter the catalyst, ligand and isopropyl metal compound may be added concurrently to the solution, and may be added sequentially. The adding order of the catalyst, ligand and isopropyl metal compound when sequentially adding thereof is not particularly limited, but it is preferable that the mixture of catalyst and ligand is added first and then the isopropyl metal compound is added sequentially. Also, the catalyst, ligand and isopropyl metal compound may be mixed in advance and added.

In the mixing order case (B), the isopropyl metal compound is dissolved in a solvent and thereafter the catalyst, ligand and 4-halogenated-3-methylphenol may be added to the solution concurrently and may be added sequentially. The adding order of the catalyst, ligand and 4-halogenated-3-methylphenol when sequentially adding thereof is not particularly limited. Also, the catalyst, ligand and 4-halogenated-3-methylphenol may be mixed in advance and added.

In the mixing order case (C), the catalyst and ligand are mixed in a solvent, and thereafter the 4-halogenated-3-methylphenol and isopropyl metal compound may be added to the mixture concurrently and may be added sequentially. The adding order of the 4-halogenated-3-methylphenol and isopropyl metal compound when adding sequentially thereof is not particularly limited, but it is preferable that the 4-halogenated-3-methyl phenol and isopropyl metal compound are sequentially added in this order. Also, the 4-halogenated-3-methylphenol and isopropyl metal compound may be mixed in advance and added.

The reaction may be a batch method and may be a continuous method. If the reaction is conducted by the batch method, it is usually conducted by using a batch reactor having stirring wings. If the catalyst fixed to a solid support is used in order to conduct the reaction by the continuous method, the reaction may be conducted in a flow type continuous reactor in which the catalyst is the fixed bed. The producing method of the present invention is capable of producing the 4-isopropyl-3-methylphenol at high conversion rate, so that the step of separating the catalyst and ligand from the reaction solution may be simplified if the catalyst is fixed to the reactor as the fixed bed. The 4-isopropyl-3-methylphenol with high productivity and purity may be obtained thereby.

The conversion rate of the reaction in the present invention is not particularly limited, but usually 70 mol % or more, preferably 80 mol % or more, more preferably 90 mol % or more, further more preferably 95 mol % or more, particularly preferably 98 mol % or more, and most preferably 99 mol % or more. The reaction selectivity is high in the producing method of the present invention, so that the reaction may be conducted at the above-described conversion rate by optimizing the raw material, catalyst, and production conditions.

Here, the conversion rate signifies the reaction rate of a raw material 4-halogenated-3-methylphenol being converted to the 4-isopropyl-3-methylphenol. Incidentally, as described later, the conversion rate may signify the total amount of both the 4-isopropyl-3-methylphenol and the 4-normalpropyl-3-methylphenol, if the 4-normalpropyl-3-methylphenol is produced as a byproduct by the producing method of the present invention.

The 4-isopropyl-3-methylphenol may be isolated and refined by a general method. Specifically, deposition by a solvent substitution, recrystallization, and extraction may be conducted in appropriate combination.

The producing method of the present invention has high reaction selectivity, so that the 4-isopropyl-3-methylphenol to be obtained has only small amount of impurity, odor and coloration. Accordingly, the load to the refinement is outstandingly reduced compared with a conventional method.

(7) 4-isopropyl-3-methylphenol

The producing method of the present invention has high reaction selectivity, so that the 4-isopropyl-3-methylphenol with high purity may be obtained by optimizing the raw material, catalyst, and production conditions (including refinement). The purity of the 4-isopropyl-3-methylphenol to be produced by the producing method of the present invention is not particularly limited, but is usually 70 mass % or more, preferably 80 mass % or more, more preferably 90 mass % or more, further more preferably 95 mass % or more, particularly preferably 98 mass % or more, and most preferably 99 mass % or more. Incidentally, here, the purity of the 4-isopropyl-3-methylphenol does not include a solvent.

The producing method of the present invention has high reaction selectivity, so that the 4-isopropyl-3-methylphenol that does not substantially contain an isomer may be obtained. The content of the isomer included in the 4-isopropyl-3-methylphenol is not particularly limited, but the content of the isomer based on the amount of the 4-isopropyl-3-methylphenol is usually 5 mass % or less, preferably 3 mass % or less, more preferably 2 mass % or less, further more preferably 1 mass % or less, particularly preferably 0.5 mass % or less, and most preferably detection limit or less. Incidentally, here, the isomer signifies the total amount of o-thymol, m-thymol, and vic-thymol.

The 4-isopropyl-3-methylphenol to be produced by the producing method of the present invention may contain a 4-normalpropyl-3-methylphenol as a byproduct in some cases. In other words, the 4-isopropyl-3-methylphenol composition (mixture) containing the 4-normalpropyl-3-methylphenol may be presumed to be the one obtained by the producing method of the present invention.

The content of the 4-normalpropyl-3-methylphenol included in the 4-isopropyl-3-methylphenol composition (mixture) to be produced by the producing method of the present invention is not particularly limited, but the content of the 4-normalpropyl-3-methylphenol based on the amount of the 4-isopropyl-3-methylphenol is usually 10 mass % or less, preferably 5 mass % or less, more preferably 2 mass % or less, and further more preferably 1 mass % or less. The lower limit of the content of the 4-normalpropyl-3-methylphenol is not limited, but usually is 0.1 mass % or more. The producing method of the present invention has high reaction selectivity, so that the 4-isopropyl-3-methylphenol that does not substantially contain or contain only small amount of isomer may be obtained.

Incidentally, the production ratio of the 4-isopropyl-3-methylphenol and the 4-normalpropyl-3-methylphenol may be controlled by the adding order of each raw material and the reaction conditions. Accordingly, the content of 4-normalpropyl-3-methylphenol may be positively increased; the 4-normalpropyl-3-methylphenol may be produced in the range that exceeds the upper limit, which is specifically at 100 mass % or less, and at 200 mass % or less furthermore.

(8) Use

The 4-isopropyl-3-methylphenol to be produced by the producing method of the present invention may be used as agents such as an antibacterial agent, bactericidal agent, and antiseptic. Also, the composition including 4-isopropyl-3-methylphenol to be produced by the producing method of the present invention may be used as products such as medicaments, quasi-drugs and cosmetics.

B. Antibacterial Composition and Bactericidal Composition

The antibacterial composition and bactericidal composition of the present invention features the configuration that includes the 4-isopropyl-3-methylphenol produced in accordance with the above-described producing method. The composition contains the 4-isopropyl-3-methylphenol as an agent such as an antibacterial agent and bactericidal agent.

The antibacterial composition and bactericidal composition may contain various components other than the 4-isopropyl-3methylphenol. Each component may be appropriately selected in accordance with the use of the antibacterial composition and bactericidal composition. Also, the content of the 4-isoproply-3-methylphenol may be appropriately selected in accordance with the use of the antibacterial composition and bactericidal composition.

The characteristic of the antibacterial composition and bactericidal composition of the present invention is not particularly limited; examples thereof may include a liquid such that the 4-isopropyl-3-methylphenol is dissolved or dispersed in water, alcohol, other organic solvent or mixed solution of these, and a resin composition (solid) such that the 4-isopropyl-3-methylphenol is contained in or coated with a thermoplastic resin, thermoplastic elastomer, rubber, or thermosetting resin. Also, the composition may be in the forms of paste, wax, gel, and gum, besides liquid and solid.

The antibacterial composition and bactericidal composition of the present invention may be used for the products such as medicaments, quasi-drugs and cosmetics; specific examples thereof may include a detergent composition, antiperspiration composition, antifungal composition, and cosmetic composition. Further, the composition may be used for an antibacterial commodity.

Incidentally, the present invention is not limited to the embodiments. The embodiments are exemplification, and any is included in the technical scope of the present invention if it has substantially the same constitution as the technical idea described in the claim of the present invention and offers similar operation and effect thereto.

EXAMPLES

The present invention will be described in further details with reference to examples as follows. Incidentally, the present invention is not at all limited to the following examples.

Example 1

Prepared in a flask were 11.2 mg (0.05 mmol) of palladium acetate (Pd(OAc)$_2$), 41.1 mg (0.1 mmol) of 2-dicyclohexylphosphino-2',6'-dimethoxybiphenyl (SPhos), and 1870 mg (10 mmol) of 4-bromo-3-methylphenol, and subjected to nitrogen substitution.

Next, 50 mL of dehydrated and deoxidized THF was injected into the flask to make the solution temperature to be 20° C. Then, 0.5 mol/L THF solution of 3768 mg (20 mmol) of isopropyl zinc bromide was slowly dropped to the mixed solution and stirred so as to maintain the system temperature at 20° C. After dropping the whole amount, stirring was continued for day and night while maintaining 20° C.

The obtained reacted solution was analyzed by a gas chromatography (detector: FID) and as the result, the product was constituted with 97.7 mass % of a 4-isopropyl-3-methylphenol, 1.6 mass % of a 4-normalpropyl-3-methylphenol, 0.7 mass % of an m-cresol, and a trace amount of other impurity (excluding the solvent THF; hereinafter applies the same). Also, the conversion rate of the 4-bromo-3-methylphenol was 99 mol %.

Incidentally, as the result of analyzing the reacted solution with the gas chromatography by taking out the solution with time, the composition of the reacted solution was almost stable as the above constitution after 3 hours passed from dropping whole amount of the THF solution of isopropyl zinc bromide.

Example 2

The reaction was conducted in the same manner as in Example 1 except that a 2-dicyclohexylphosphino-2',6'-bis (N,N-dimethylamino)biphenyl (CPhos) was used instead of the 2-dicyclohexylphosphino-2',6'-dimethoxybiphenyl (SPhos).

The obtained reacted solution was analyzed by a gas chromatography (detector: FID); as the result, the product was constituted with 96.6 mass % of a 4-isopropyl-3-methylphenol, 2.4 mass % of a 4-normalpropyl-3-methylphenol, 1.0 mass % of an m-cresol, and a trace amount of other impurity. Also, the conversion rate of the 4-bromo-3-methylphenol was 99 mol %.

Incidentally, as the result of analyzing the reacted solution with the gas chromatography by taking out the solution with time, the composition of the reacted solution was almost stable as the above constitution after 3 hours passed from dropping whole amount of the THF solution of isopropyl zinc bromide.

Example 3

The reaction was conducted in the same manner as in Example 1 except that the used amount of the palladium acetate (Pd(OAc)$_2$) was changed to 45.0 mg (0.2 mmol) and 188.7 mg (0.4 mmol) of a 2-dicyclohexylphosphino-2',6'-diisopropoxybiphenyl (RuPhos) was used instead of the 2-dicyclohexylphosphino-2',6'-dimethoxybiphenyl (SPhos).

The obtained reacted solution was analyzed by a gas chromatography (detector: FID); as the result, the product was constituted with 95.9 mass % of a 4-isopropyl-3-methylphenol and 4.1 mass % of a 4-normalpropyl-3-methylphenol; no m-cresol was detected, and other impurity was a trace amount. Also, the conversion rate of the 4-bromo-3-methylphenol was 95.4 mol %.

Incidentally, as the result of analyzing the reacted solution with the gas chromatography by taking out the solution with time, the composition of the reacted solution was almost stable as the above constitution after 3 hours passed from dropping whole amount of the THF solution of isopropyl zinc bromide.

Example 4

Prepared in a flask was 5 mol/L THF solution of 2826 mg (15 mmol) of isopropyl zinc bromide, which was subjected to nitrogen substitution and thereafter made the solution temperature to be 20° C.

Next, the solution in which 11.2 mg (0.05 mmol) of a palladium acetate (Pd(OAc)$_2$), 41.1 mg (0.1 mmol) of a 2-dicyclohexylphosphino-2',6'-dimethoxybiphenyl (SPhos), and 1870 mg (10 mmol) of a 4-bromo-3-methylphenol were dissolved together in advance in 50 mL of dehydrated and deoxidized THF, was slowly dropped to the flask and stirred. The whole amount of the solution was dropped while maintaining the temperature inside the system to be 20° C., and the stirring was continued for day and night while maintaining 20° C.

The obtained reacted solution was analyzed by a gas chromatography (detector: FID); as the result, the product was constituted with 98.0 mass % of 4-isopropyl-3-methylphenol and 2.0 mass % of a 4-normalpropyl-3-methylphenol; no m-cresol was detected and other impurity was a trace amount. Also, the conversion rate of the 4-bromo-3-methylphenol was 93 mol %.

Incidentally, as the result of analyzing the reacted solution with the gas chromatography by taking out the solution with time, the composition of the reacted solution was almost stable as the above constitution after 3 hours passed from dropping whole amount of the THF solution of isopropyl zinc bromide.

Example 5

Prepared in a flask were 472.2 mg (10 tablets, 10 mmol as SPhos) of a solid support that contains a palladium acetate (Pd(OAc)$_2$) and 2-dicyclohexylphosphino-2',6'-dimethoxybiphenyl (SPhos) at the molar ratio of 1:2 (manufactured by Sigma-Aldrich Co. LLC., product name: palladium acetate ChemDose tablet), and 93.6 mg (5 mmol) of a 4-bromo-3-methylphenol, and subjected to nitrogen substitution.

Next, 16 mL of dehydrated and deoxidized THF was added to the flask and the temperature of the solution was made to be 40° C. Then, 2.5 mL of THF solution of an isopropyl zinc bromide (12.5 mmol as the isopropyl zinc bromide) was dropped to the mixed solution and stirred taking 1 hour. After dropping the whole amount, stirring was continued for 1 hour while maintaining 40° C. The solid support was easily removed from the obtained reacted solution by filtering.

The obtained reacted solution was analyzed by a gas chromatography (detector: FID); as the result, the product was constituted with 59.4 mass % of a 4-isopropy-3-methylphenol, 6.3 mass % of a 4-normalpropyl-3-methylphenol, 4.6 mass % of an m-cresol, and 29.7 mass % of the raw material 4-bromo-3-methylphenol. Also, the conversion rate of the 4-bromo-3-methylphenol was 75 mol %.

SUMMARY

The results in Examples 1 to 5 are shown in Table 1. In Examples 1 to 4, the production was conducted by using a catalyst dissolved in a solvent; it was confirmed that the 4-isopropyl-3-methylphenol was produced at extremely high conversion rate (reaction selectivity) in each case.

Also, in Example 5, the catalyst was fixed and made to be a fixed bed reactor; it was also confirmed that the intended 4-isopropyl-3-methylphenol may be produced at high conversion rate. Further, the 4-isopropyl-3-methylphenol with high purity may be efficiently produced by making the apparatus to be a flow type continuous reactor so as to supply the raw material continuously and to collect the 4-isopropyl-3-methylphenol to be obtained.

Incidentally, the adding order (A) and (B) in Table 1 refers to the following orders.

(A) The solution including isopropyl metal compound was added to the solution including 4-halogenated-3-methylphenol, catalyst, and ligand.

(B) The solution including 4-halogenated-3-methylphenol, catalyst, and ligand was added to the solution including isopropyl metal compound.

Also, BMP, i-PMP, and n-PMP in Table 1 respectively refer to the 4-bromo-3-methylphenol, 4-isopropyl-3-methylphenol, and 4-normalpropyl-3-methylphenol.

TABLE 1

| | Producing method | | | Product (mass %) | | | | | Conversion rate |
|---|---|---|---|---|---|---|---|---|---|
| | Catalyst form | Ligand | Adding order | BMP | i-PMP | n-PMP | Metacresol | Others | (mol %) |
| Example 1 | Liquid | SPhos | (A) | 0 | 97.7 | 1.6 | 0.7 | 0 | 99 |
| Example 2 | Liquid | CPhos | (A) | 0 | 96.6 | 2.4 | 1.0 | 0 | 99 |
| Example 3 | Liquid | RuPhos | (A) | 0 | 95.9 | 4.1 | 0 | 0 | 95 |
| Example 4 | Liquid | SPhos | (B) | 0 | 98.0 | 2.0 | 0 | 0 | 93 |
| Example 5 | Solid | SPhos | (A) | 29.7 | 59.4 | 6.3 | 4.6 | 0 | 75 |

Incidentally, the series of the examples are shown as the specific embodiments in the present invention, but these are mere exemplifications and should not be understood in the limited manner. All the various modifications clear to an ordinary skilled person in the art are planned to be in the scope of the present invention. This application is based on Japanese Patent Application (No. 2014-132880), the date of application being Jun. 27, 2014, and the descriptions therein are taken herein as references.

The invention claimed is:

1. A producing method for a 4-isopropyl-3-methylphenol, wherein a 4-halogenated-3-methylphenol is reacted with an isopropyl metal compound under presence of a catalyst, a ligand and a solvent; and
    the ligand is one kind or a mixture of two or more kinds selected from 2-dicyclohexylphosphino-2',6'-diisopropoxybiphenyl, 2-dicyclohexylphosphino-2',6'-dimethoxybiphenyl, and 2-dicyclohexylphosphino-2',4',6'-triisopropylbiphenyl.

2. The producing method for a 4-isopropyl-3-methylphenol according to claim 1, wherein the 4-halogenated-3-methylphenol is a 4-bromo-3-methylphenol.

3. The producing method for a 4-isopropyl-3-methylphenol according to claim 1, wherein the isopropyl metal compound is an isopropyl zinc bromide.

4. The producing method for a 4-isopropyl-3-methylphenol according to claim 1, wherein the catalyst includes one kind or two kinds or more selected from palladium, nickel, ruthenium, iron and copper.

5. The producing method for a 4-isopropyl-3-methylphenol according to claim 1, wherein the ligand is one kind or a mixture of two kinds selected from a 2-dicyclohexylphosphino-2',6'-diisopropoxybiphenyl, and a 2-dicyclohexylphosphino-2',6'-dimethoxybiphenyl.

6. The producing method for a 4-isopropyl-3-methylphenol according to claim 1, wherein the solvent is a solvent including ether that is capable of dissolving the isopropyl metal compound.

7. The producing method for a 4-isopropyl-3-methylphenol according to claim 1, wherein the catalyst and the ligand are mixed with the solvent, and then the 4-halogenated-3-methylphenol and the isopropyl metal compound are added to the mixed solution.

8. The producing method for a 4-isopropyl-3-methylphenol according to claim 1, wherein at least either of the catalyst and the ligand is fixed to a solid support.

* * * * *